United States Patent
Martz et al.

(10) Patent No.: US 10,934,411 B2
(45) Date of Patent: Mar. 2, 2021

(54) CURABLE COMPOSITIONS CONTAINING 1,1-DI-ACTIVATED VINYL COMPOUNDS THAT CURE BY PERICYCLIC REACTION MECHANISMS

(71) Applicant: PPG Industries Ohio, Inc., Cleveland, OH (US)

(72) Inventors: Jonathan Thomas Martz, Valencia, PA (US); Michael Andrew Zalich, Wexford, PA (US); Aditya Lakshmi Narasimha Raju Gottumukkala, Monroeville, PA (US); Stuart Damon Hellring, Pittsburgh, PA (US); Ronnie Albertus Johannes Peskens, Haarlem (NL)

(73) Assignee: PPG Industries Ohio, Inc., Cleveland, OH (US)

( * ) Notice: Subject to any disclaimer, the term of this patent is extended or adjusted under 35 U.S.C. 154(b) by 200 days.

(21) Appl. No.: 15/722,443

(22) Filed: Oct. 2, 2017

(65) Prior Publication Data

US 2018/0094115 A1  Apr. 5, 2018

Related U.S. Application Data

(60) Provisional application No. 62/565,835, filed on Sep. 29, 2017, provisional application No. 62/402,029, filed on Sep. 30, 2016.

(51) Int. Cl.

| | | |
|---|---|---|
| *C07C 55/08* | (2006.01) | |
| *C07C 57/13* | (2006.01) | |
| *C08K 5/053* | (2006.01) | |
| *C08K 5/092* | (2006.01) | |
| *C08K 5/00* | (2006.01) | |
| *C08K 5/09* | (2006.01) | |
| C07C 13/20 | (2006.01) | |
| G01R 33/46 | (2006.01) | |
| C09J 11/06 | (2006.01) | |
| G01N 24/08 | (2006.01) | |

(52) U.S. Cl.
CPC ........... *C08K 5/0025* (2013.01); *C07C 55/08* (2013.01); *C07C 57/13* (2013.01); *C08K 5/053* (2013.01); *C08K 5/09* (2013.01); *C08K 5/092* (2013.01); *C07C 13/20* (2013.01); *C09J 11/06* (2013.01); *G01N 24/088* (2013.01); *G01R 33/46* (2013.01)

(58) Field of Classification Search
CPC ........ C08K 5/0025; C08K 5/053; C08K 5/09; C08K 5/092; C07C 55/08; C07C 57/13; C07C 13/20; C09J 11/06; G01N 24/088; G01N 33/46

See application file for complete search history.

(56) References Cited

U.S. PATENT DOCUMENTS

| | | | | |
|---|---|---|---|---|
| 2,212,506 A | * | 8/1940 | Bachman | C07C 69/593 560/203 |
| 2,610,963 A | * | 9/1952 | Doak | C08F 222/12 526/292.4 |
| 2,610,964 A | * | 9/1952 | Ewart | C08F 236/04 526/91 |
| 3,197,318 A | | 7/1965 | Halpern et al. | |
| 3,660,263 A | | 5/1972 | Auletta et al. | |
| 4,382,109 A | | 5/1983 | Olson et al. | |
| 4,452,861 A | | 6/1984 | Okamoto et al. | |
| 4,528,349 A | * | 7/1985 | D'Alelio | C07D 209/48 526/262 |
| 4,740,534 A | | 4/1988 | Matsuda et al. | |
| 4,885,191 A | | 12/1989 | Podszun et al. | |
| 5,321,112 A | | 6/1994 | Olson | |
| 5,639,828 A | | 6/1997 | Briggs et al. | |
| 5,723,275 A | | 3/1998 | Wang et al. | |
| 6,517,940 B1 | | 2/2003 | Millero et al. | |
| 8,609,885 B2 | | 12/2013 | Malofsky et al. | |
| 8,884,051 B2 | | 11/2014 | Malofsky et al. | |
| 9,108,914 B1 | | 8/2015 | Malofsky et al. | |
| 9,181,365 B2 | | 11/2015 | Malofsky et al. | |
| 9,221,739 B2 | | 12/2015 | Malofsky et al. | |
| 9,334,430 B1 | | 5/2016 | Stevenson et al. | |
| 9,416,091 B1 | | 8/2016 | Sullivan et al. | |
| 9,567,475 B1 | | 2/2017 | Palsule et al. | |
| 2003/0030170 A1 | | 2/2003 | Abe et al. | |
| 2003/0042142 A1 | | 3/2003 | Yamoto et al. | |
| 2005/0171273 A1 | | 8/2005 | Ledwidge et al. | |
| 2012/0027974 A1 | * | 2/2012 | Skillman | B65D 1/12 428/35.8 |
| 2014/0275419 A1 | | 9/2014 | Ward et al. | |

(Continued)

FOREIGN PATENT DOCUMENTS

| | | |
|---|---|---|
| CN | 102796909 A | 11/2012 |
| CN | 103520771 A | 1/2014 |

(Continued)

OTHER PUBLICATIONS

International Search Report and Written Opinion for International Patent Application No. PCT/EP2017/044010, dated Oct. 30, 2017.
International Search Report and Written Opinion for International Patent Application No. PCT/EP2017/043995, dated Jul. 11, 2017.
International Search Report and Written Opinion for International Patent Application No. PCT/EP2017/044041, dated Nov. 7, 2017.
International Search Report and Written Opinion for International Patent Application No. PCT/EP2017/044001, dated Oct. 30, 2017.
International Search Report and Written Opinion for International Patent Application No. PCT/EP2017/044032, dated Nov. 6, 2017.

(Continued)

*Primary Examiner* — Irina S Zemel
*Assistant Examiner* — Jeffrey S Lenihan
(74) *Attorney, Agent, or Firm* — K&L Gates LLP

(57) ABSTRACT

Curable compositions containing a compound comprising a conjugated diene group and a 1,1-di-activated vinyl compound are described. The curable compositions can cure by pericyclic reaction mechanisms.

42 Claims, 2 Drawing Sheets

(56) References Cited

U.S. PATENT DOCUMENTS

| | | | |
|---|---|---|---|
| 2014/0288230 A1 | 9/2014 | Malofsky et al. | |
| 2014/0329980 A1 | 11/2014 | Malofsky et al. | |
| 2015/0056879 A1 | 2/2015 | Malofsky et al. | |
| 2015/0361283 A1 | 12/2015 | Malofsky et al. | |
| 2016/0068618 A1 | 3/2016 | Sullivan et al. | |
| 2019/0153244 A1 | 5/2019 | Puodziukynaite et al. | |
| 2019/0160739 A1 | 5/2019 | Olson et al. | |
| 2019/0161620 A1 | 5/2019 | Zalich et al. | |
| 2019/0161637 A1 | 5/2019 | Olson | |
| 2019/0161640 A1 | 5/2019 | Gottumukkala et al. | |

FOREIGN PATENT DOCUMENTS

| | | | |
|---|---|---|---|
| CN | 104312246 A | | 1/2015 |
| CN | 105536049 A | | 5/2016 |
| CN | 105585879 | | 5/2016 |
| DE | 19909212 A1 | * | 9/2000 |
| EP | 0046088 A1 | | 2/1982 |
| EP | 0327129 A1 | | 8/1989 |
| EP | 0829756 A2 | | 7/1999 |
| EP | 3042939 A1 | | 7/2016 |
| JP | 2008019350 | | 1/2008 |
| JP | 2013100599 | | 5/2013 |
| JP | 2014077024 | | 5/2014 |
| KR | 20140145084 A | | 12/2014 |
| WO | 0032709 A1 | | 6/2000 |
| WO | 2008086033 A1 | | 7/2008 |
| WO | 2013036347 A1 | | 3/2013 |
| WO | 2013059473 A2 | | 4/2013 |
| WO | 2013149173 A1 | | 10/2013 |
| WO | 2015165808 A1 | | 11/2015 |
| WO | 2017210415 | | 12/2017 |
| WO | 2018022810 | | 2/2018 |
| WO | WO 2018/022804 A1 | | 2/2018 |

OTHER PUBLICATIONS

International Search Report and Written Opinion for International Patent Application No. PCT/EP2017/044014, dated Oct. 27, 2017.
International Search Report and Written Opinion for International Patent Application No. PCT/EP2017/044005, dated Nov. 3, 2017.
Triallyl Isocyanurate TAIC Product Description, Mitsubishi International PolymerTrade Corporation, http://www.michem.com/triallyl_isocyanurate.html, 6 pages, Apr. 4, 2019.

* cited by examiner

CURABLE COMPOSITIONS CONTAINING 1,1-DI-ACTIVATED VINYL COMPOUNDS
THAT CURE BY PERICYCLIC REACTION
MECHANISMS

CROSS REFERENCE TO RELATED APPLICATIONS

This application claims the benefit of U.S. Provisional Application No. 62/402,029 filed on Sep. 30, 2016, and U.S. Provisional Application No. 62/565,835, filed on Sep. 29, 2017, both of which are incorporated by reference herein in their entirety.

FIELD

The present disclosure relates to curable compositions containing a compound comprising a conjugated diene group and a 1,1-di-activated vinyl compounds.

BACKGROUND

Curable compositions include coating compositions and adhesive and sealant compositions. Coating compositions are used to form coating layers that are applied to a wide variety of substrates to provide color and/or other visual effects, corrosion resistance, abrasion resistance, chemical resistance, or other protective properties. Adhesive and sealant compositions are used to bond together two or more articles, fill cracks or other defects in articles, or provide protective barrier properties to articles. It would be advantageous to provide curable compositions, including coating, adhesive, and sealant compositions, characterized by novel curing mechanisms and properties.

SUMMARY

The present disclosure generally relates to curable compositions, including coating, adhesive, and sealant compositions, comprising a conjugated diene group-containing compound and a 1,1-di-activated vinyl compound. The present disclosure also relates to coating, adhesive, or sealant systems comprising a reaction product of a conjugated diene group-containing compound and a 1,1-di-activated vinyl compound. The present disclosure also relates to processes for applying the curable compositions to substrates; processes for treating the coating, adhesive, or sealant systems; and articles comprising the coating, adhesive, or sealant systems deposited on a surface of the articles.

A curable composition may comprise a compound comprising a conjugated diene group and a 1,1-di-activated vinyl compound, or a multifunctional form thereof, or a combination thereof. A process for applying the curable composition to a substrate comprises applying the curable composition over at least a portion of a substrate and curing the curable composition. The curing comprises a crosslinking reaction between (1) the compound comprising a conjugated diene group and (2) the 1,1-di-activated vinyl compound, or a multifunctional form thereof, or a combination thereof.

A coating, adhesive, or sealant system comprises a coating, adhesive, or sealant layer applied to at least a portion of a substrate, wherein the coating, adhesive, or sealant layer comprises a Diels-Alder addition reaction product of (1) a resin or other compound comprising pendant and/or terminal conjugated diene groups and (2) a 1,1-di-activated vinyl compound, or a multifunctional form thereof, or a combination thereof. A process for treating the coating, adhesive, or sealant system comprises applying heat, radiation, pressure, or a catalyst composition, or a combination of any thereof, to the coating, adhesive, or sealant system. The application of the heat, radiation, pressure, and/or a catalyst composition results in a retro-Diels-Alder reaction that breaks the addition reaction bonds between the resin or other compound and the 1,1-di-activated vinyl compound and reverses cure of the coating, adhesive, or sealant layer.

It is understood that the invention described in this specification is not necessarily limited to the examples provided in this Summary.

BRIEF DESCRIPTION OF THE DRAWINGS

Various features and characteristics of the invention described in this specification may be better understood by reference to the accompanying figures, in which.

Figure 1:
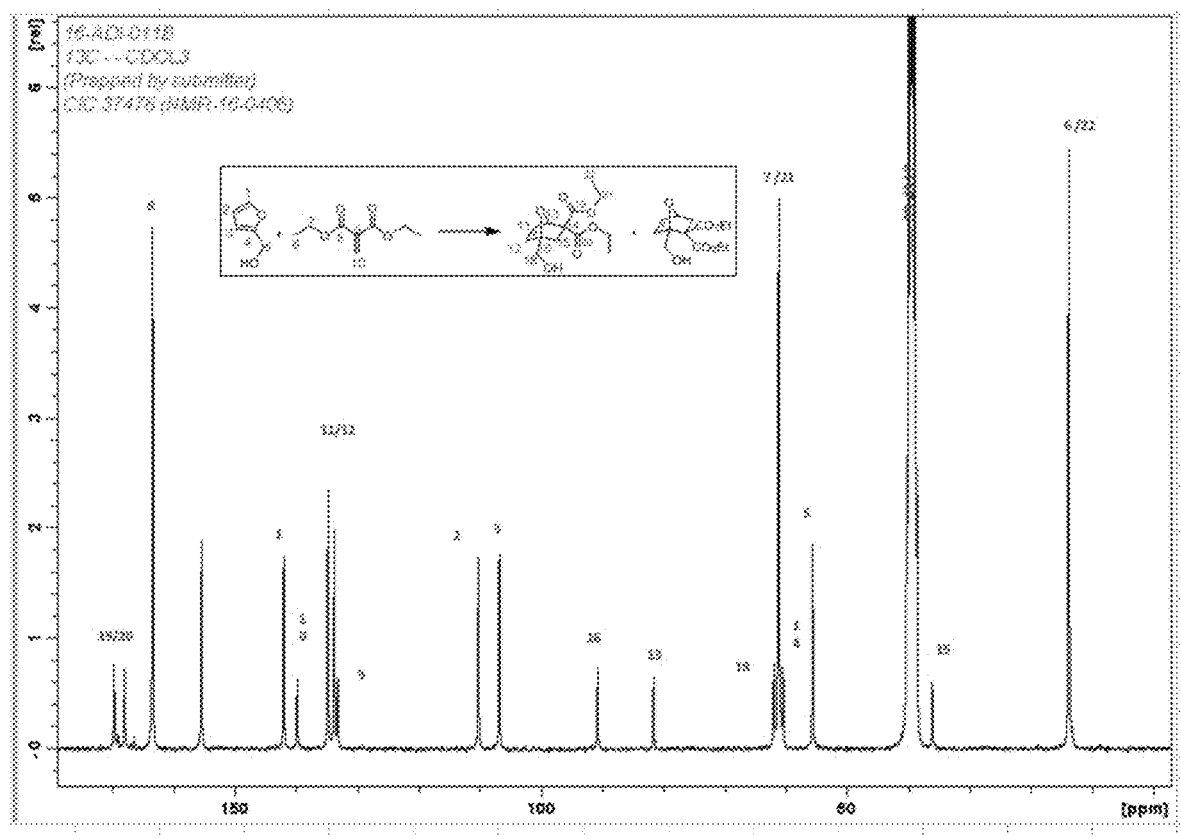
FIG. 1 is a $^{13}$C NMR spectrum of a reaction product mixture confirming the formation of Diels-Alder cycloaddition reaction products in connection with Example 1.

The reader will appreciate the foregoing features and characteristics, as well as others, upon considering the following detailed description of the invention according to this specification.

DETAILED DESCRIPTION

As used in this specification, particularly in connection with coating, adhesive, or sealant layers or films, the terms "on," "onto," "over," and variants thereof (e.g., "applied to," "formed over," "deposited over," "provided over," "located over," and the like), mean applied, formed, deposited, provided, or otherwise located over a surface of a substrate, but not necessarily in contact with the surface of the substrate. For example, a coating layer "applied over" or "applied to" a substrate does not preclude the presence of one or more other coating layers of the same or different composition located between the applied coating layer and the substrate. Likewise, a second coating layer "applied over" or "applied to" a first coating layer does not preclude the presence of one or more other coating layers of the same or different composition located between the applied second coating layer and the applied first coating layer.

As used in this specification, the terms "polymer" and "polymeric" means prepolymers, oligomers, and both homopolymers and copolymers. As used in this specification, "prepolymer" means a polymer precursor capable of further reactions or polymerization by one or more reactive groups to form a higher molecular mass or cross-linked state.

As used in this specification, the prefix "poly" refers to two or more. For example, a "polyfunctional" molecule (whether a polymer, monomer, or other compound) comprises two or more reactive functional groups such as hydroxyl groups, amine groups, mercapto groups, carbamate groups, and the like. More specifically, "polyol" means a compound comprising two or more hydroxyl groups, "polyamine" means a compound comprising two or more amine groups, and "polythiol" means a compound comprising two or more mercapto groups.

A polyfunctional compound such as a polyol, polyamine, or polythiol may be a polymer, but does not have to be a polymer, and may comprise, for example, non-polymeric compounds. A polymeric polyol, polymeric polyamine, or polymeric polythiol respectively comprises two or more pendant and/or terminal hydroxyl, amine, or mercapto functional groups on the polymer molecules. A "pendant group" refers to a group that comprises an offshoot from the side of a polymer backbone and which does not comprise part of the polymer backbone, whereas "terminal group" refers to a group on an end of a polymer backbone and which comprises part of the polymer backbone.

Additionally, the terms polyol, polyamine, and polythiol may encompass compounds comprising combinations of different types of functional groups. For example, a compound comprising two or more hydroxyl groups and two or more amine groups may be referred to as a polyol, a polyamine, or a polyol/polyamine. Furthermore, polyol, polyamine, and polythiol, compounds may comprise either or both the neutral functional groups (hydroxyl, amine, mercapto, or carbamate) and/or a salt of an ionized form of the functional group (e.g., alkoxide salts, ammonium salts, and the like).

As used in this specification, the term "1,1-di-activated vinyl compound" means a compound comprising a vinyl group having two electron withdrawing groups (EWG) covalently bonded to one of the π-bonded carbons and no substituents covalently bonded to the other π-bonded carbon (i.e., -EWG-C(=CH$_2$)-EWG-), wherein the electron withdrawing groups independently comprise halogen groups, haloalkyl groups, carbonyl-containing groups (e.g., esters, amides, aldehydes, ketones, acyl halides, carboxylic/carboxylate groups), cyano groups, sulfonate groups, ammonium groups, quaternary amine groups, or nitro groups. The term "multifunctional form of [ . . . ]" refers to a substance derived from more than one molecule of the respective compound that comprises more than one of the respective functional groups of said compound. The term "multifunctional form of a 1,1-di-activated vinyl" means a compound comprising two or more 1,1-di-activated vinyl groups covalently bonded in one molecule. For instance, a dialkyl methylene malonate is an example of a 1,1-di-activated vinyl compound, and a transesterification adduct of a dialkyl methylene malonate and a polyol is an example of a multifunctional form of a dialkyl methylene malonate.

The present disclosure provides curable compositions, including coating compositions, adhesive compositions, and sealant compositions, comprising (1) a compound comprising a conjugated diene group and (2) a 1,1-di-activated vinyl compound, or a multifunctional form thereof, or a combination thereof. The curable compositions can be applied to at least a portion of a substrate and cured. The term "cured," as used in this specification, refers to the condition of a coating, adhesive, or sealant composition in which at least one of the components of the composition has chemically reacted to form new covalent bonds in the composition. Accordingly, the terms "cure" and "curing" refer to the chemical crosslinking of components in a composition applied as a layer (e.g., film, bead, or other mass) on a substrate. The terms "cure" and "curing" do not encompass solely physical drying of coating compositions through solvent or carrier evaporation. The curing of the curable compositions comprises a crosslinking addition reaction between (1) the compound comprising a conjugated diene group and (2) the 1,1-di-activated vinyl compound, or a multifunctional form thereof, or a combination thereof.

In some examples, the crosslinking reaction comprises a pericyclic addition reaction, such as, for example, a cycloaddition reaction, between (1) the compound comprising a conjugated diene group and (2) the 1,1-di-activated vinyl compound, or a multifunctional form thereof, or a combination thereof. In some examples, the crosslinking reaction comprises a Diels-Alder reaction between (1) the compound comprising a conjugated diene group and (2) the 1,1-di-activated vinyl compound. As used in this specification, a "Diels-Alder reaction" refers to a cycloaddition reaction between a conjugated diene compound and an ethylenically unsaturated dienophile such as, for example, a 1,1-di-substituted vinyl compound, as depicted below in scheme (1).

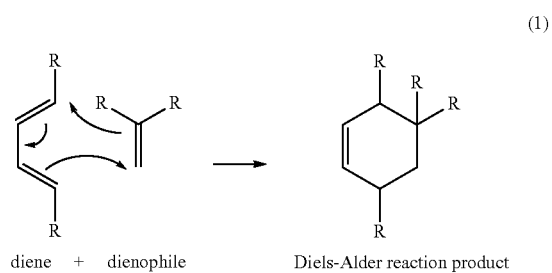

(1)

diene + dienophile     Diels-Alder reaction product

Similarly, as used in this specification, a "retro-Diels-Alder reaction" refers to the reverse cycloaddition reaction between a conjugated diene compound and an ethylenically unsaturated dienophile such as, for example, 1,1-di-substituted vinyl compound, wherein the Diels-Alder reaction product re-forms the conjugated diene compound and the ethylenically unsaturated dienophile, as depicted below in scheme (2).

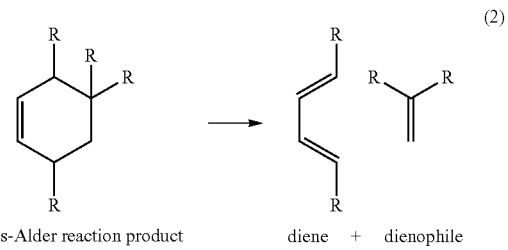

(2)

Diels-Alder reaction product     diene + dienophile

A forward Diels-Alder reaction between (1) a compound comprising a conjugated diene group and (2) a 1,1-di-activated vinyl compound, or a multifunctional form thereof, or a combination thereof, forms covalent crosslinks between components in the curable compositions that can be reversed through a retro-Diels-Alder reaction mechanism. For example, a cured coating, adhesive, or sealant system formed from the curable composition can be treated by applying heat, radiation (e.g., infrared radiation), pressure, and/or a catalyst composition to the cured coating, adhesive, or sealant composition. The application of the heat, radiation, pressure, and/or a catalyst composition can initiate and/or catalyze a retro-Diels-Alder reaction that breaks the cycloaddition bonds between the compound comprising the conjugated diene group and the 1,1-di-activated vinyl compound, or multifunctional form thereof, or combination thereof. Thus, the crosslinking reaction between (1) a compound comprising a conjugated diene group and (2) a 1,1-di-activated vinyl compound, or a multifunctional form thereof, or a combination thereof, is reversible and the cured/crosslinked composition can be selectively uncured/uncrosslinked.

It is understood that the terms "Diels-Alder reaction" and "retro-Diels-Alder reaction" encompass the various types of Diels-Alder reactions including, for example, hetero-Diels-Alder reactions, aza-Diels-Alder reactions, and inverse electron-demand Diels-Alder reactions, and the retro-reactions thereof.

In some examples, the pericyclic crosslinking reaction between (1) the compound comprising a conjugated diene group and (2) the 1,1-di-activated vinyl compound, or a multifunctional form thereof, or a combination thereof (e.g., a Diels-Adler reaction or cycloaddition reaction) occurs in a cascade with another chemical transformation or multiple other chemical transformations. For example, a crosslinking reaction can comprise a pericyclic reaction cascade that incorporates a Diels-Alder reaction coupled with at least one other pericyclic reaction.

The 1,1-di-activated vinyl compound can comprise one or more methylene dicarbonyl compounds, dihalo vinyl compounds, dihaloalkyl disubstituted vinyl compounds, or cyanoacrylate compounds, or multifunctional forms of any thereof, or combinations of any thereof. Examples of 1,1-di-activated vinyl compounds and multifunctional forms thereof that can be used in the crosslinker and coating compositions are described in U.S. Pat. Nos. 8,609,885; 8,884,051; 9,108,914; 9,181,365; and 9,221,739, which are incorporated by reference into this specification. Additional examples of 1,1-di-activated vinyl compounds and multifunctional forms thereof that can be used in the crosslinker and coating compositions are described in U.S. Publication Nos. 2014/0288230; 2014/0329980; and 2016/0068618, which are incorporated by reference into this specification.

The curable compositions can comprise a 1,1-di-activated vinyl compound comprising a methylene malonate. Methylene malonates are compounds having the general formula (I):

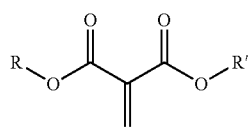

wherein R and R' may be the same or different and may represent nearly any substituent or side-chain, such as substituted or unsubstituted alkyl or aryl groups. For example, the curable compositions can comprise a dialkyl methylene malonate, a diaryl methylene malonate, a multifunctional form of a dialkyl methylene malonate, or a multifunctional form of a diaryl methylene malonate, or a combination of any thereof.

A multifunctional form of a methylene malonate can comprise a transesterification adduct of the methylene malonate and a polyol. A multifunctional form of a methylene malonate can thus have the general formula (II):

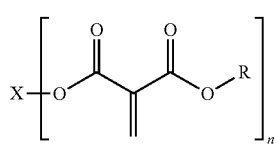

wherein n is greater than one, X is a polyol residue and each R may be the same or different, as described above. In some examples, a multifunctional form of a methylene malonate can comprise a transesterification adduct of the methylene malonate and a diol, and thus have the general formula (III):

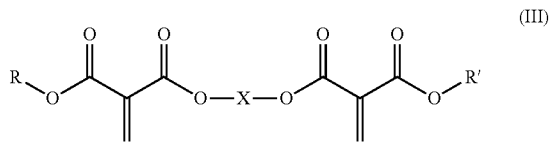

wherein X is a diol residue and R and R' may be the same or different, as described above.

Polyols that are suitable for the production of a transesterification adduct with a methylene malonate include, for example, polymeric polyols (such as polyether polyols, polyester polyols, acrylic polyols, and polycarbonate polyols) and monomeric polyols (such as alkane polyols, including alkane diols such as 1,5-pentanediol and 1,6-hexanediol). Examples of transesterification adducts of methylene malonates and polyols that may be used in the coating compositions are described in U.S. Publication No. 2014/0329980 and U.S. Pat. No. 9,416,091, which are incorporated by reference herein.

In some examples, the curable compositions can comprise dimethyl methylene malonate (D3M), a multifunctional form of D3M, or both. In some examples, the curable compositions can comprise diethyl methylene malonate (DEMM), a multifunctional form of DEMM, or both. The multifunctional forms of D3M or DEMM can comprise transesterification adducts of D3M or DEMM and a polyol, such as, for example, 1,5-pentanediol or 1,6-hexanediol.

In some examples, the curable compositions can comprise a combination of a dialkyl methylene malonate and a multifunctional form of a dialkyl methylene malonate. The curable compositions can comprise, for example, DEMM and a multifunctional form of DEMM comprising a transesterification adduct of DEMM and at least one polyol. The DEMM can be transesterified with polyol comprising, for example, an alkane diol such as 1,5-pentanediol or 1,6-hexanediol.

The compound comprising a conjugated diene group can comprise a polymeric and/or a non-polymeric compound. Non-polymeric compounds comprising a conjugated diene group can include cross-linking agents (such as, for example, polyisocyanates, as described below) that react with film-forming resins or binder resins in the curable compositions to crosslink the resins and introduce the diene functionality into the curing resins, or chain extenders (such as, for example, non-polymeric polyols, polyamines, or polythiols) that react with the resins to extend the constituent polymer chains and introduce the diene functionality into the curing resins. In this manner, the reaction between the introduced diene functionality and the 1,1-di-activated vinyl compound can provide a secondary curing mechanism that is selectively reversible, as described above.

The conjugated diene groups can comprise cyclic conjugated diene groups or open-chain conjugated diene groups covalently incorporated into the polymeric and/or non-polymeric compounds. Cyclic conjugated diene groups comprise at least two conjugated π-bonds that are part of a ring structure, including heteroatomic ring structures. Examples of cyclic conjugated diene groups include, for example, cyclopentadiene groups, thiophene groups, pyrrole groups, and furan groups. Open-chain conjugated diene groups comprise at least two conjugated π-bonds that are not part of a ring structure. Examples of open-chain conjugated diene groups include, for example, alkyl-substituted diene groups such as 1,3-butadiene groups, 1,3-pentadiene groups, and isoprene groups. In some examples, open-chain conjugated diene groups can have the following general formula (IV):

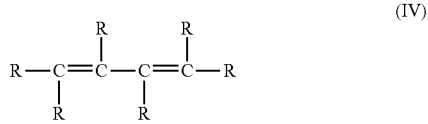

wherein each R independently comprises hydrogen, an alkyl substituent, or an aryl substituent, optionally substituted with heteroatoms such as oxygen, nitrogen, or sulfur, or other functional groups such as hydroxyl groups, amino groups, mercapto groups, isocyanate groups, or the like.

In some examples, the curable compositions comprise a polymer resin comprising pendant and/or terminal conjugated diene groups. The polymer resin can comprise pendant and/or terminal open-chain conjugated diene groups, pendant and/or terminal cyclic conjugated diene groups, or combination thereof, covalently attached to the constituent polymer chains comprising the resin. In examples comprising pendant and/or terminal cyclic conjugated diene groups, the resin can comprise pendant and/or terminal cyclopentadiene groups, thiophene groups, pyrrole groups, or furan groups, or combinations of any thereof. In examples comprising pendant and/or terminal open-chain conjugated diene groups, the resin can comprise pendant and/or terminal alkyl-substituted diene groups, such as 1,3-butadiene groups, 1,3-pentadiene groups, or isoprene groups, or other open-chain conjugated diene groups having the following general formula (V):

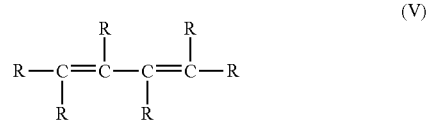

wherein each R independently comprises hydrogen or an alkyl radical, optionally substituted with heteroatoms such as oxygen, nitrogen, or sulfur, or other functional groups such as hydroxyl groups, amino groups, mercapto groups, isocyanate groups, or the like, provided, however, that at least one R includes the covalent linkage to the polymer resin in a pendant and/or terminal position.

In the curable compositions comprising a polymer resin comprising pendant and/or terminal conjugated diene groups, the resin can comprise a reaction product of (1) a polyisocyanate and (2) a conjugated diene compound comprising an active hydrogen group (e.g., a hydroxyl group, a primary or secondary amino group, or a thiol group).

The polyisocyanate can comprise polyisocyanate compounds such as, for example, aliphatic polyisocyanates, cycloaliphatic polyisocyanates, araliphatic polyisocyanates, or aromatic polyisocyanates, or a combination of any thereof. In some examples, the polyisocyanate compounds can comprise aliphatic polyisocyanates and/or cycloaliphatic polyisocyanates. Examples of suitable aliphatic and cycloaliphatic polyisocyanates include 4,4-methylenebisdicyclohexyl diisocyanate (hydrogenated MDI), hexamethylene diisocyanate (HDI), isophorone diisocyanate (IPDI), methylenebis(cyclohexyl isocyanate), trimethyl hexamethylene diisocyanate (TMDI), meta-tetramethylxylylene diisocyanate (TMXDI), and cyclohexylene diisocyanate (hydrogenated XDI). Examples of suitable aromatic polyisocyanates include toluene diisocyanate (TDI) (i.e., 2,4-toluene diisocyanate, 2,6-toluene diisocyanate, or a mixture thereof), diphenylmethane-4,4-diisocyanate (MDI), naphthalene-1,5-diisocyanate (NDI), 3,3-dimethyl-4,4-biphenylene diisocyanate (TODI), crude TDI (i.e., a mixture of TDI and an oligomer thereof), polymethylenepolyphenyl polyisocyanate, crude MDI (i.e., a mixture of MDI and an oligomer thereof), xylylene diisocyanate (XDI), and phenylene diisocyanate.

A polymer resin comprising pendant and/or terminal conjugated diene groups can comprise a reaction product of a conjugated diene compound comprising an active hydrogen group and a diisocyanate compound and/or a polyisocyanate compound comprising a diisocyanate reaction product (such as, for example, reaction products of the diisocyanates described above) comprising urethane groups, urea groups, uretdione groups, uretonimine groups, isocyanurate groups, iminooxadiazine dione groups, oxadiazine trione groups, carbodiimide groups, acyl urea groups, biuret groups, and/or allophanate groups. Examples of such diisocyanate reaction products include diisocyanate adducts and diisocyanate oligomers. In some examples, the polymer resin can comprise a reaction product of a conjugated diene compound comprising an active hydrogen group and a polyisocyanate component comprising at least one of HDI, IPDI, or hydrogenated MDI, or adducts or oligomers of HDI, IPDI, or hydrogenated MDI, or combinations of any thereof.

The conjugated diene compound comprising an active hydrogen group can comprise any compound having a covalently attached hydroxyl group, primary or secondary amino group, or thiol group and a covalently attached conjugated diene group, as described above, including cyclic conjugated diene groups and open-chain conjugated diene groups. Such compounds include, but are not limited to, hydroxyl-substituted, amino-substituted, or mercapto-substituted derivatives of cyclopentadiene, thiophene, pyrrole, furan, 1,3-butadiene, 1,3-pentadiene, or isoprene, or other cyclic or open-chain conjugated diene-containing compounds. Examples of such compounds include, but are not limited to, furfuryl alcohol, furfuryl amine, furfuryl mercaptan, furylethanol, furylethylamine, furylethylmercaptan, thienylmethanol, thienylmethylamine, thienylmethylthiol, thienylethanol, thienylethylamine, thienylethylthiol, 1H-pyrrol-2-methanol, 1H-pyrrol-2-methylamine, 1H-pyrrol-2-methylthiol, 2,3-butadiene-1-ol, 2,3-butadiene-1-amine, 2,3-butadiene-1-thiol, 1,3-butadiene-2-ol, 1,3-butadiene-2-amine, 1,3-butadiene-2-thiol, 3,4-pentadiene-1-ol, 3,4-pentadiene-1-amine, and 3,4-pentadiene-1-thiol.

In the curable compositions comprising a polymer resin comprising pendant and/or terminal conjugated diene groups, the resin can comprise a reaction product of (1) a polyfunctional polymeric resin and (2) a conjugated diene compound comprising an isocyanate group.

The polyfunctional polymeric resins include polymeric resins comprising pendant and/or terminal hydroxyl, amine, and/or mercapto groups, such as, for example, polyether polyols, polyester polyols, acrylic polyols, polycarbonate polyols, polyether polyamines, polyester polyamines, acrylic polyamines, polycarbonate polyamines, polyether polythiols, polyester polythiols, acrylic polythiols, polycarbonate polythiols, and combinations of any thereof. Additional polyfunctional polymeric resins include any polyfunctional polymeric resins that incorporate hydroxyl, amine, or mercapto groups, or combinations of any thereof, including for example, polyurethane resin, a polyurea resin, an acrylic resin, a polyester resin, a polycarbonate resin, a polyether resin, a polythioether resin, a polycarbamate resin, a polysiloxane resin, an epoxy resin, a melamine resin, a phenolic resin (e.g., a phenol formaldehyde resin), aminoplast resins (urea-formaldehyde and/or melamine-formaldehyde), or a composite resin comprising a polymer comprising two or more backbone functionalities, or a combination of any thereof.

The conjugated diene compound comprising an isocyanate group can comprise any compound having a covalently attached isocyanate group and a covalently attached conjugated diene group, as described above, including cyclic conjugated diene groups and open-chain conjugated diene groups. Such compounds include, but are not limited to, isocyanate-substituted derivatives of cyclopentadiene, thiophene, pyrrole, furan, 1,3-butadiene, 1,3-pentadiene, or isoprene, or other cyclic or open-chain conjugated diene-containing compounds. Examples of such compounds include, but are not limited to, furfuryl isocyanate, 2-thienyl isocyanate, and compounds comprising a covalently bound isocyanate group and butadiene or pentadiene group.

As described above, the curable compositions can comprise a compound comprising a conjugated diene group, which can comprise a polymeric compound, such as the resins described above, and/or a non-polymeric compound. In some examples, a non-polymeric compound comprising a conjugated diene group can comprise a reaction product of (1) a polyfunctional non-polymeric compound comprising a hydroxyl, amine, and/or mercapto group and (2) a conjugated diene compound comprising an isocyanate group as described above.

Examples of non-polymeric polyol compounds include, but are not necessarily limited to, glycols such as ethylene glycol, diethylene glycol, triethylene glycol, 1,2-propylene glycol, 1,3-butylene glycol, tetramethylene glycol, hexamethylene glycol, neopentyl glycol, pentaerythritol, and combinations of any thereof. Other suitable hydroxyl-containing polyfunctional non-polymeric compounds include, but are not limited to, 1,5-pentandiol, 1,6-hexanediol, cyclohexanedimethanol, 2-ethyl-1,6-hexanediol, 1,4-butanediol, 1,3-propanediol, 1,4-butanediol, trimethylol propane, 1,2,6-hexanetriol, glycerol, and combinations of any thereof. Additionally, non-polymeric amino alcohols that can be reacted with a conjugated diene compound comprising an isocyanate group to produce a non-polymeric compound comprising a conjugated diene group include, but are not limited to, ethanolamine, propanolamine, butanolamine, and combinations of any thereof.

Examples of non-polymeric polyamine compounds that can be reacted with a conjugated diene compound comprising an isocyanate group to produce a non-polymeric compound comprising a conjugated diene group include, for example, diamines such as, for example, ethylenediamine, hexamethylenediamine, 1,2-propanediamine, 2-methyl-1,5-penta-methylenediamine, 2,2,4-trimethyl-1,6-hexanediamine, isophoronediamine, diaminocyclohexane, xylylenediamine, 1,12-diamino-4,9-dioxadodecane, and combinations of any thereof. Other suitable non-polymeric and polymeric polyamine compounds include the Jeffamine® products available from Huntsman Chemical Company.

Examples of non-polymeric and polymeric polythiol compounds that can be reacted with a conjugated diene compound comprising an isocyanate group to produce a non-polymeric compound comprising a conjugated diene group include, for example, resins and compounds produced by the esterification of a polyol with a mercapto organic acid. Examples of suitable polyols include the polyols described above, and examples of suitable mercapto organic acids include thioglycolic acid and mercaptopropionic acid. Examples of non-polymeric polythiol compounds include, but are not limited to, glyceryl dithioglycolate, glyceryl trithioglycolate, glycol dimercaptoacetate, pentaerythritol tetramercaptoacetate, glycol di-(3-mercaptopropionate), pentaerythritol tetra(3-mercaptopropionate), dipentaerythritol hexa(3-mercaptopropionate), trimethylolpropane tris-(thioglycolate), pentaerythritol tetrakis-(thioglycolate), ethyleneglycol dithioglycolate, trimethylolpropane tris-(βthiopropionate), pentaerythritol tetrakis-(β-thiopropionate), dipentaerythritol poly(β-thiopropionate). Other suitable non-polymeric and polymeric polythiol compounds include the Thiocure® products available from Bruno Bock Chemische Fabrik GmbH & Co. KG.

In the curable compositions comprising a polymer resin comprising pendant and/or terminal conjugated diene groups, the resin can comprise an acrylic resin comprising a reaction product of monomers including cyclic conjugated diene groups and polymerizable vinyl groups. Such compounds include, but are not limited to, vinyl-substituted derivatives of cyclopentadiene, thiophene, pyrrole, or furan or other cyclic conjugated diene-containing compounds. Examples of such compounds include, but are not limited to, acrylate-substituted and methacrylate-substituted derivatives of cyclopentadiene, thiophene, pyrrole, or furan or other cyclic conjugated diene-containing compounds (e.g., furfuryl (meth)acrylate, furylethyl (meth)acrylate, thienylmethyl (meth)acrylate, thienylethyl (meth)acrylate, or (meth)acrylate-substituted derivatives of pyrrole or cyclopentadiene).

Additionally, diene groups can be indirectly incorporated into acrylic polymer resins. For example, acrylic polymers can be prepared from monomer mixtures comprising glycidyl methacrylate and the resulting epoxy-functional acrylic resins can be subsequently reacted with diene-containing carboxylic acids, such as, for example, 2,4-hexadienoic acid (sorbic acid). Additional acids that can be reacted with epoxy-functional acrylic resins include conjugated drying oil acids such as 9,11-octadecadienoic acid (e.g., 9-11® Acids, commercially available from Vertellus Performance Materials Inc. In another example, acrylic polymers can be prepared from monomer mixtures comprising isocyanate-functional and vinyl-functional monomers such as, for example, isocyanatoethyl methacrylate, m-isopropenyl-alpha, alpha-dimethylbenzyl isocyanate (m-TMI), or allyl isocyanate, and the resulting isocyanate-functional acrylic resins can be subsequently reacted with diene-containing alcohols, such as, for example, 2,4-hexadien-1-ol (sorbic alcohol).

In some examples, the curable compositions can comprise at least two polymeric resins: (1) a polymeric resin comprising pendant and/or terminal conjugated diene groups and (2) a polymeric resin comprising pendant and/or terminal 1,1-di-activated vinyl groups. In such examples, the 1,1-di-activated vinyl compound is covalently attached to the polymers of the second resin to form the 1,1-di-activated vinyl groups. The covalent attachment of 1,1-di-activated vinyl compounds to polymeric polyols (including the polymeric polyols described above) at pendant and/or terminal positions can be performed using transesterification procedures as described, for example, in U.S. Publication No.

2014/0329980 and U.S. Pat. No. 9,416,091, which are incorporated by reference herein.

The curable compositions can include additional materials such as additional resins, colorants (organic or inorganic pigments or dyes), plasticizers, abrasion resistant particles, anti-oxidants, hindered amine light stabilizers, UV light absorbers and stabilizers, surfactants, flow and surface control agents, thixotropic agents, solvents and co-solvents, reactive diluents, catalysts, reaction inhibitors, and other customary auxiliaries in the paint, coating, adhesive, and sealant industries.

The curable compositions can be applied to substrates and cured to form a coating, adhesive, or sealant system. The coating, adhesive, or sealant system comprises a coating, adhesive, or sealant layer applied over at least a portion of a substrate. In this regard, the term "layer" includes, but is not limited to, applied coating films and encompasses other structural forms of applied curable composition such as adhesive or sealant films or beads (e.g., caulking type products). The coating, adhesive, or sealant layer comprises a Diels-Alder addition reaction product of (1) a polymeric resin or non-polymeric compound comprising conjugated diene groups (as described above, e.g., resins comprising pendant and/or terminal conjugated diene groups on a polymer chain) and (2) a 1,1-di-activated vinyl compound, or a multifunctional form thereof, or a combination thereof (as described above). The coating, adhesive, or sealant layer may exhibit properties such as intumescence, delamination, or self-healing upon the application of heat, radiation (e.g., infrared radiation or microwave radiation), pressure, and/or a catalyst composition (e.g., Lewis acid or Lewis base catalysts). In some examples, the coating, adhesive, or sealant layer may contain a photoredox catalyst that can be activated by exposure to radiation (e.g., ultraviolet radiation).

As described above, the curable compositions can be cured through a Diels-Alder crosslinking reaction between (1) the compound (e.g., polymeric resin) comprising a conjugated diene group and (2) the 1,1-di-activated vinyl compound, or a multifunctional form thereof, or a combination thereof, to form cured coating, adhesive, or sealant layers. At least a portion of the covalent crosslinks between these components in the cured coating, adhesive, or sealant layers can be reversed through a retro-Diels-Alder reaction mechanism that is initiated and/or catalyzed by the application of heat, radiation, pressure, and/or a catalyst composition to the cured material and which breaks the cycloaddition bonds between the crosslinked components. Thus, the crosslinking reaction between (1) the compound comprising a conjugated diene group and (2) the 1,1-di-activated vinyl compound, or a multifunctional form thereof, or a combination thereof, is reversible and the cured/crosslinked composition can be selectively uncured/uncrosslinked.

The selective uncuring/uncrosslinking of the cured material formed from the curable compositions can facilitate the intumescence, delamination, or self-healing properties upon the application of heat, radiation, pressure, a catalyst composition, or a combination of any thereof. Intumescence refers to the swelling (increasing the volume and decreasing the density) of a material upon heat exposure. Intumescent materials are used in passive fire protection applications. The cured materials (e.g., coating, adhesive, or sealant layers) formed from the curable compositions may function as intumescent materials by undergoing a retro-Diels-Adler reaction at elevated temperatures (e.g., upon application of heat or infrared radiation) which at least partially reverses the curing/crosslinking of the material, rendering the material more thermoplastic and facilitating the intumescent expansion of the material. Accordingly, the curable compositions may be useful in intumescent coatings, adhesives, or sealants in passive fire protection applications such as, for example, cellulosic fire prevention.

The cured materials (e.g., coating, adhesive, or sealant layers) formed from the curable compositions may exhibit at least partial delamination or otherwise facilitate the stripping of the cured material from substrates by undergoing a retro-Diels-Adler reaction at elevated temperatures (e.g., upon application of heat or infrared radiation), or by the application of a catalyst composition, which at least partially reverses the curing/crosslinking of the material. The at least partially reversed curing/crosslinking of the material may decrease the adhesion of the material to a substrate and the internal cohesion of the material, which may result in partial delamination or otherwise decrease the manual labor required to strip the material from a substrate. Additionally, the reversed curing/crosslinking of the material may render the material more thermoplastic, which may further decrease the manual labor required to strip the material from a substrate. Accordingly, the curable compositions may be useful in temporary coatings applications or as adhesives for substrates such as decorative wall paper and interior walls.

The cured materials (e.g., coating layers) formed from the curable compositions may exhibit self-healing properties by undergoing a retro-Diels-Adler reaction at elevated temperatures (e.g., upon application of heat or infrared radiation), or by the application of a catalyst composition, which at least partially reverses the curing/crosslinking of the material. The at least partially reversed curing/crosslinking of the material may render the material more thermoplastic and capable of flowing to fill-in and "heal" mechanical damage (e.g., scratches) in coating layers. The "healed" coating layer can then undergo a forward Diels-Adler reaction to re-crosslink and re-cure the coating. The application of heat, radiation, pressure, or a catalyst composition, or a combination of any thereof, to promote the retro-Diels-Adler reaction and "healing" of a damaged coating film can be targeted to the location of the damage, where the balance of the undamaged coating film remains in the crosslinked/cured state. Accordingly, the curable compositions may be useful in topcoat applications.

The invention thus includes a process for treating a coating, adhesive, or sealant system comprising applying heat, radiation, pressure, and/or a catalyst composition to the coating, adhesive, or sealant system. The application of the heat, radiation, pressure, and/or catalyst composition results in a retro-Diels-Alder reaction that breaks the addition reaction bonds between (1) the compound comprising a conjugated diene group (e.g., a polymeric resin comprising pendent and/or terminal conjugated diene group) and the 1,1-di-activated vinyl compound, or a multifunctional form thereof, or a combination thereof (e.g., a non-polymeric compound or polymeric resin comprising covalently attached 1,1-di-activated vinyl groups). The application of the heat, radiation, pressure, and/or catalyst composition reverses cure of the coating, adhesive, or sealant layer, as described above, and in some examples, the coating, adhesive, or sealant layer becomes intumescent, delaminates, becomes hand peel-able, or exhibits self-healing properties.

The present invention further includes an article comprising a coating, adhesive, or sealant system formed from the curable compositions described in this specification. For example, the curable compositions can be applied to a wide range of substrates including vehicle components and components of free-standing structures such as buildings, bridges, or other civil infrastructures. More specific substrates include, but are not limited to, automotive substrates (e.g., body panels and other parts and components), industrial substrates, aircraft components, watercraft components, packaging substrates (e.g., food and beverage cans), wood flooring and furniture, apparel, electronics (e.g., housings and circuit boards), glass and transparencies, sports equipment (e.g., golf balls, and the like), appliances (e.g., dish washing machines, clothes washing machines, clothes drying machines), interior walls and wall paper. Substrates can be, for example, metallic or non-metallic. Metallic substrates include, but are not limited to, tin, steel (including electrogalvanized steel, cold rolled steel, hot-dipped galvanized steel, among others), aluminum, aluminum alloys, zinc-aluminum alloys, steel coated with a zinc-aluminum alloy, and aluminum plated steel. Non-metallic substrates include polymeric, plastic, polyester, polyolefin, polyamide, cellulosic, polystyrene, polyacrylic, poly(ethylene naphthalate), polypropylene, polyethylene, nylon, EVOH, polylactic acid, other "green" polymeric substrates, poly(ethyleneterephthalate) (PET), polycarbonate, polycarbonate acrylobutadiene styrene (PC/ABS), polyamide, wood, veneer, wood composite, particle board, fiberboard, cement, concrete, brick, stone, paper, cardboard, textiles, leather (both synthetic and natural), glass or fiberglass composites, carbon fiber composites, mixed fiber (e.g., fiberglass and carbon fiber) composites, and the like. The substrate can be one that has been already treated in some manner, such as to impart visual and/or color effect, a protective pretreatment or primer coating layer, or other coating layer, and the like.

WORKING EXAMPLES

The following working examples are intended to further describe the invention. It is understood that the invention described in this specification is not necessarily limited to the examples described in this section.

Example 1: Diels-Alder Reaction of Conjugated Diene Compound and 1,1-Di-Activated Vinyl Compound A high density polyethylene (HDPE) reaction flask equipped with a Teflon coated stir-bar was charged under a blanket of nitrogen with 2.0 grams of furfuryl alcohol and 3.4 grams of a mixture of diethyl methylene malonate and a transesterification adduct of diethyl methylene malonate and 1,5-pentanediol (as described in U.S. Publication No. 2014/0329980). The reaction flask was capped and provided with a vent to prevent pressure build-up. The flask was placed on a magnetic stir-plate and allowed to stir for 24 hours under ambient conditions, during which time at least some of the following reactions are believed to have occurred.

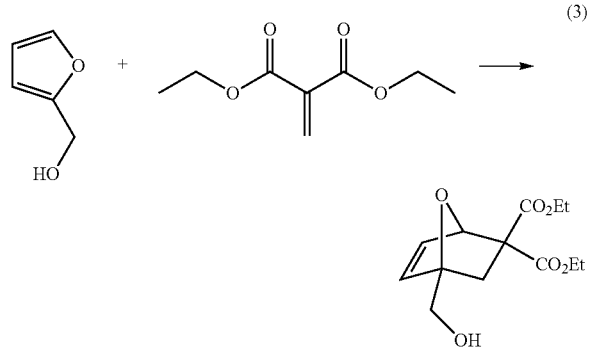

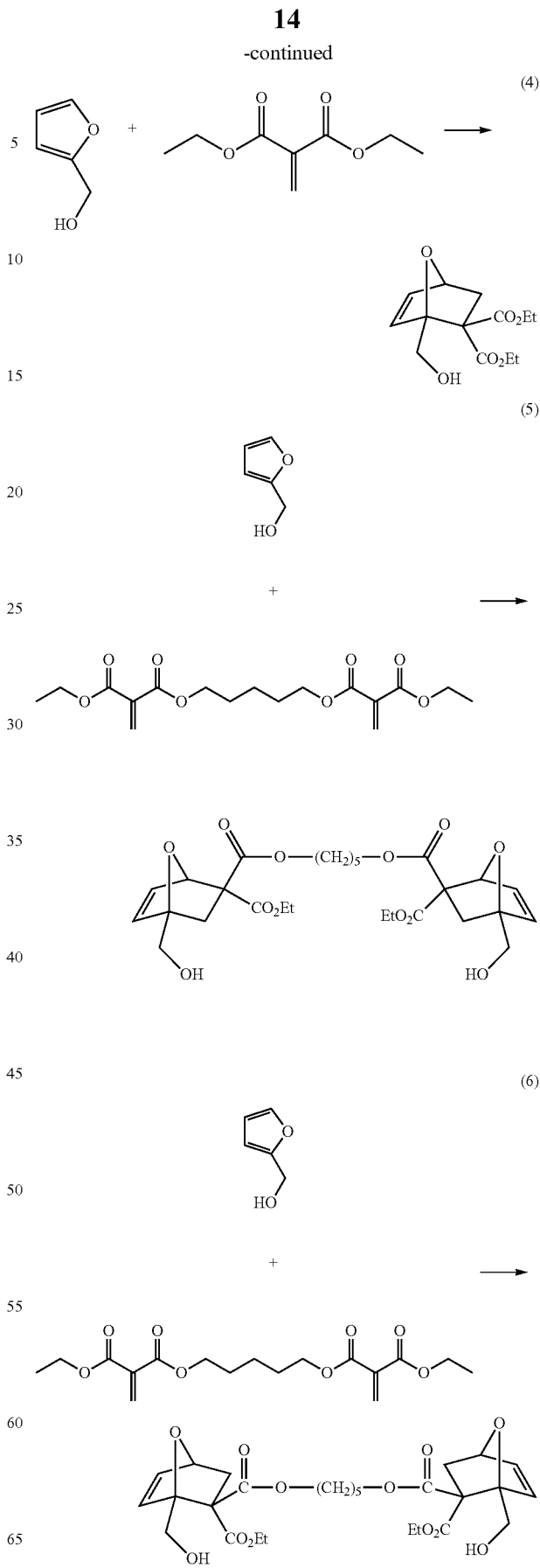

-continued

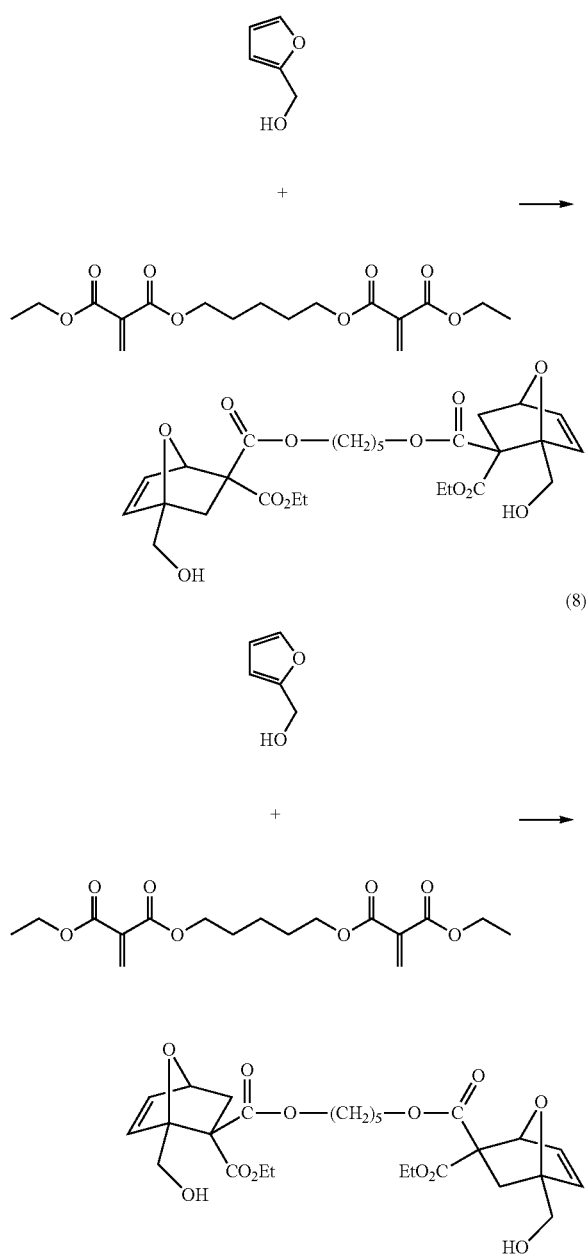

(7)

(8)

The reaction procedure described above was repeated at 120° C. and 140° C. After the 24 hour reaction period, the reaction mixtures were sampled and evaluated for the formation of products by $^{13}$C NMR. FIG. 1 shows the $^{13}$C NMR spectrum for the reaction mixture after reaction at 120° C. The signals at 81.5 ppm and 90.7 ppm in the $^{13}$C NMR spectrum shown in FIG. 1 (labeled as 13 and 16, respectively) are characteristic of the oxygen-bridged, substituted cyclohexene reaction product, which confirmed the formation of Diels-Alder cycloaddition reaction products. The yield of the reactions was estimated to be 25% from the $^{13}$C NMR spectrum. The $^{13}$C NMR spectra for the reaction mixtures after reaction at room temperature and 140° C. also confirmed the formation of the Diels-Alder cycloaddition reaction products.

Example 2: Preparation of Diene-Functional Resin

A 4-neck round-bottom glass flask was pacified by wiping with a 2% (w/w) solution of methane sulfonic acid in ethanol, rinsing with acetone, and drying in ambient air. The pacified flask was equipped with a mechanical overhead stirrer, heating mantle, and condenser. To the flask was added 91.5 grams (0.3 moles, 1 equivalent) of Desmodur® N 3600 (a hexamethylene diisocyanate trimer (isocyanurate), commercially available from Covestro AG), 60 grams of methyl isobutyl ketone (0.6 moles), and 0.1 grams of dibutyltin dilaurate. The mixture was allowed to stir under a steady stream of nitrogen gas and warmed to 50° C. A solution of furfuryl alcohol (50 grams, 0.51 moles, 1.02 equivalents) in methyl isobutyl ketone (20 grams) was added dropwise into the stirring reaction mixture. Once the addition was complete, the reaction mixture was warmed to 80° C. and held until the disappearance of all the isocyanate functionality was confirmed by titration. The reaction mixture was then cooled to room temperature and the resulting resin is referred to below as the "Diene Resin."

Figure 2:
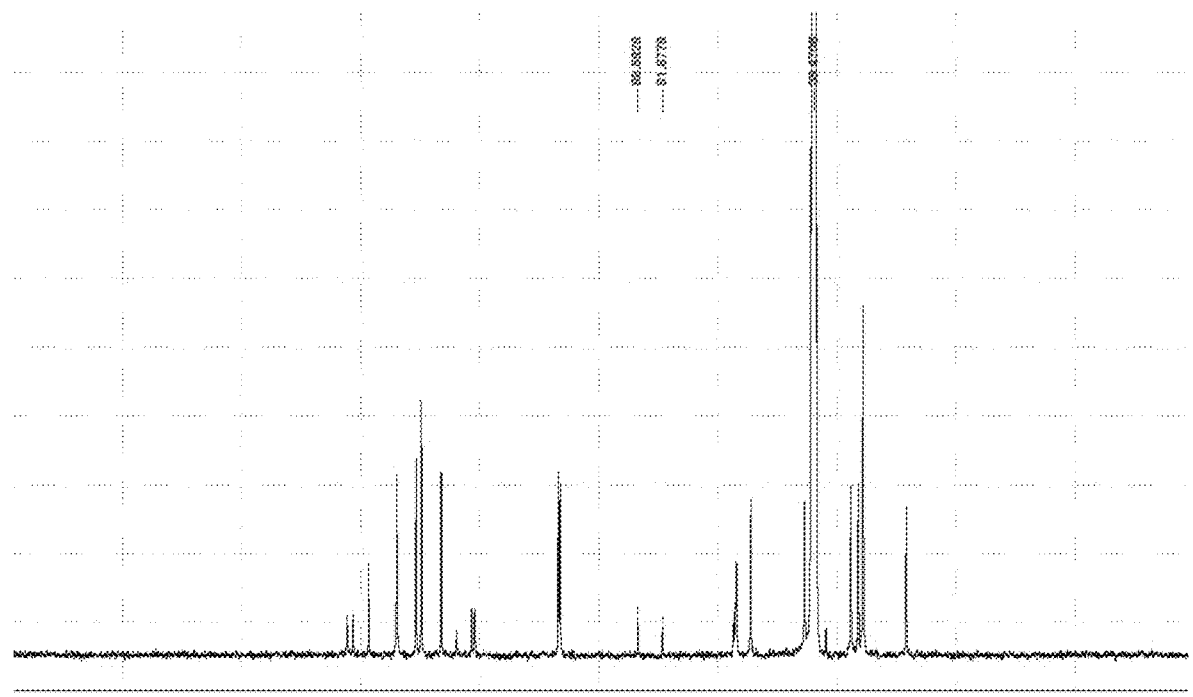
FIG. 2 is a $^{13}$C NMR spectrum of a reaction product mixture confirming the formation of Diels-Alder cycloaddition reaction products in connection with Example 3.

Example 3: Diels-Alder Reaction of Diene Resin and 1,1-Di-Activated Vinyl Compound 60 grams of the Diene Resin (Example 2) was dissolved into 60 grams of methyl isobutyl ketone and placed into a separate 4-neck round bottom flask equipped with a stir-blade, mantle, and condenser. The resulting mixture was warmed to 50° C. in the flask. Diethyl methylene malonate (26 grams) was added into the flask via an addition funnel. The resulting reaction mixture was then warmed to 80° C. and held for 4 hours, after which it was cooled back to room temperature and concentrated in vacuum. The reaction mixture was sampled and evaluated for the formation of products by $^{13}$C NMR. FIG. 2 shows the $^{13}$C NMR spectrum for the reaction mixture. The signals at 81.8 ppm and 88.6 ppm in the $^{13}$C NMR spectrum shown in FIG. 2 are characteristic of the oxygen-bridged, substituted cyclohexene reaction product, which confirmed the formation of Diels-Alder cycloaddition reaction products.

Example 4: Curable Composition Comprising Conjugated Diene Resin and 1,1-Di-Activated Vinyl Compound The Diene Resin (Example 2) was combined in equal parts by weight with a mixture of diethyl methylene malonate and a transesterification adduct of diethyl methylene malonate and 1,5-pentanediol (as described in U.S. Publication No. 2014/0329980). The mixture was applied over a pacified glass panel (2% (w/w) methane sulfonic acid in ethanol wipe, acetone rinse, and ambient air dry) using a draw down bar with a 3 mil gap. The panel was baked at 140° C. for 1 hour to produce a cured coating layer on the glass panel substrate.

An MEK double rub test was performed on the cured coating layer. The MEK double rub test reports the number of double (back-and-forth) rubs, performed by hand with a methyl ethyl ketone (MEK) soaked rag, required to dissolve the applied coating such that the substrate is visible. The double rubs were performed up to a maximum number of 100 and discontinued. The cured coating layer survived the 100 MEK double rubs with no visible damage.

ASPECTS OF THE INVENTION

Aspects of the invention include, but are not limited to, the following numbered clauses.

1. A curable composition comprising:
    a compound comprising a conjugated diene group; and
    a 1,1-di-activated vinyl compound, or a multifunctional form thereof, or a combination thereof.
2. The curable composition of clause 1, wherein the 1,1-di-activated vinyl compound comprises a methylene dicarbonyl compound, a dihalo vinyl compound, a dihaloalkyl disubstituted vinyl compound, or a cyanoacrylate compound, or a multifunctional form of any thereof, or a combination of any thereof.
3. The curable composition of clause 2, wherein the 1,1-di-activated vinyl compound comprises:
    a dialkyl methylene malonate;
    a diaryl methylene malonate;
    a multifunctional form of a dialkyl methylene malonate; or
    a multifunctional form of a diaryl methylene malonate; or
    a combination of any thereof.
4. The curable composition of clause 3, wherein the 1,1-di-activated vinyl compound comprises:
    diethyl methylene malonate; and/or
    a multifunctional form of diethyl methylene malonate comprising a transesterification adduct of diethyl methylene malonate and at least one polyol.
5. The curable composition of clause 4, wherein the transesterification adduct of diethyl methylene malonate and at least one polyol comprises a transesterification adduct of diethyl methylene malonate and a diol.
6. The curable composition of clause 5, wherein the diol comprises an alkane diol.
7. The curable composition of clause 6, wherein the alkane diol comprises 1,5-pentane diol and/or 1,6-hexanediol.
8. The curable composition of any one of clauses 1-7, wherein the compound comprising a conjugated diene groups comprises a polymer resin comprising pendant and/or terminal conjugated diene groups.
9. The curable composition of clause 8, wherein the resin comprises pendant and/or terminal open-chain conjugated diene groups.
10. The curable composition of clause 8, wherein the resin comprises pendant and/or terminal cyclic conjugated diene groups.
11. The curable composition of clause 10, wherein the resin comprises pendant and/or terminal cyclopentadiene groups.
12. The curable composition of clause 10, wherein the resin comprises pendant and/or terminal thiophene groups.
13. The curable composition of clause 10, wherein the resin comprises pendant and/or terminal pyrrole groups.
14. The curable composition of clause 10, wherein the resin comprises pendant and/or terminal furan groups.
15. The curable composition of clause 8, wherein the resin comprises a reaction product of a polyisocyanate and a conjugated diene compound comprising an active hydrogen group.
16. The curable composition of clause 8, wherein the resin comprises a reaction product of a polyol, polyamine, or polythiol and a conjugated diene compound comprising an isocyanate group.
17. The curable composition of clause 8 or clause 15, wherein the resin comprises a polyurethane resin, a polyurea resin, an acrylic resin, a polyester resin, a polycarbonate resin, a polysiloxane resin, an epoxy resin, a melamine resin, or a phenol formaldehyde resin, or a composite resin comprising a polymer comprising two or more backbone functionalities, or a combination of any thereof.
18. A coating composition comprising the curable composition of any one of clauses 1-17.
19. An adhesive or sealant composition comprising the curable composition of any one of clauses 1-17.
20. A process for applying a curable composition to a substrate comprising:
    applying the curable composition of any one of clauses 1-17 to at least a portion of a substrate; and
    curing the curable composition;
    wherein the curing comprises a crosslinking reaction between (1) the compound comprising a conjugated diene group and (2) the 1,1-di-activated vinyl compound, or a multifunctional form thereof, or a combination thereof.
21. The process of clause 20, wherein the crosslinking reaction comprises a pericyclic reaction.
22. The process of clause 20 or clause 21, wherein the crosslinking reaction comprises a cycloaddition reaction.
23. The process of any one of clauses 20-22, wherein the crosslinking reaction comprises a Diels-Alder reaction.
24. The process of any one of clauses 20-23, wherein the crosslinking reaction comprises a pericyclic reaction that occurs in a cascade with another chemical transformation.
25. A coating, adhesive, or sealant system comprising:
    a coating, adhesive, or sealant layer applied to at least a portion of a substrate, wherein the coating, adhesive, or sealant layer comprises a Diels-Alder addition reaction product of:
        a resin comprising pendant and/or terminal conjugated diene groups; and
        a 1,1-di-activated vinyl compound, or a multifunctional form thereof, or a combination thereof.
26. The coating, adhesive, or sealant system of clause 25, wherein the 1,1-di-activated vinyl compound comprises a dialkyl methylene malonate, or a multifunctional form thereof, or a combination thereof.
27. The coating, adhesive, or sealant system of clause 26, wherein the 1,1-di-activated vinyl compound comprises:
    diethyl methylene malonate; and/or
    a multifunctional form of diethyl methylene malonate comprising a transesterification adduct of diethyl methylene malonate and at least one polyol.
28. The coating, adhesive, or sealant system of clause 27, wherein the transesterification adduct of diethyl methylene malonate and at least one polyol comprises a transesterification adduct of diethyl methylene malonate and a diol.
29. The coating, adhesive, or sealant system of clause 28, wherein the diol comprises 1,5-pentane diol and/or 1,6-hexanediol.
30. The coating, adhesive, or sealant system of any one of clause 25-29, wherein the resin comprises pendant and/or terminal open-chain conjugated diene groups.
31. The coating, adhesive, or sealant system of any one of clauses 25-29, wherein the resin comprises pendant and/or terminal cyclic conjugated diene groups.
32. The coating, adhesive, or sealant system of any one of clauses 25-29 or clause 31, wherein the resin comprises pendant and/or terminal cyclopentadiene groups, thiophene groups, pyrrole groups, or furan groups, or combinations of any thereof.
33. The coating, adhesive, or sealant system of any one of clauses 25-32, wherein the resin comprises a reaction product of a polyisocyanate and a conjugated diene compound comprising an active hydrogen group.

34. The coating, adhesive, or sealant system of any one of clauses 25-32, wherein the resin comprises a reaction product of a polyol, polyamine, or polythiol and a conjugated diene compound comprising an isocyanate group.

35. The coating, adhesive, or sealant system of any one of clauses 25-34, wherein the resin comprises a polyurethane resin, a polyurea resin, an acrylic resin, a polyester resin, a polycarbonate resin, a polysiloxane resin, an epoxy resin, a melamine resin, or a phenol formaldehyde resin, or a composite resin comprising a polymer comprising two or more backbone functionalities, or a combination of any thereof.

36. The coating, adhesive, or sealant system of any one of clauses 25-35, wherein the coating, adhesive, or sealant layer exhibits intumescence, delamination, or self-healing properties upon application of heat, radiation, pressure, and/or a catalyst composition.

37. An article comprising the coating, adhesive, or sealant system of any one of clauses 25-36 deposited on a surface of the article.

38. The article of clause 37, wherein the article comprises a vehicle component, an architectural component, or a component of a free-standing structure.

39. A process for treating a coating, adhesive, or sealant system comprising:
applying heat, radiation, pressure, or a catalyst composition, or a combination of any thereof, to the coating, adhesive, or sealant system of any one of clauses 25-36;
wherein the application of the heat, radiation, pressure, and/or a catalyst composition results in a retro-Diels-Alder reaction that breaks the addition reaction bonds between the resin and the 1,1-di-activated vinyl compound and reverses cure of the coating, adhesive, or sealant layer.

40. The process of clause 39, wherein the coating, adhesive, or sealant layer becomes intumescent upon the application of the heat, radiation, pressure, and/or a catalyst composition.

41. The process of clause 39, wherein the coating, adhesive, or sealant layer delaminates upon the application of the heat, radiation, pressure, and/or a catalyst composition.

42. The process of clause 39, wherein the coating, adhesive, or sealant layer becomes hand peel-able upon the application of the heat, radiation, pressure, and/or a catalyst composition.

43. The process of clause 39, wherein the coating, adhesive, or sealant system comprises a coating layer that exhibits self-healing properties upon the application of the heat, radiation, pressure, and/or a catalyst composition.

Various features and characteristics are described in this specification to provide an understanding of the composition, structure, production, function, and/or operation of the invention, which includes the disclosed compositions, systems, and processes. It is understood that the various features and characteristics of the invention described in this specification can be combined in any suitable manner, regardless of whether such features and characteristics are expressly described in combination in this specification. The Inventors and the Applicant expressly intend such combinations of features and characteristics to be included within the scope of the invention described in this specification. As such, the claims can be amended to recite, in any combination, any features and characteristics expressly or inherently described in, or otherwise expressly or inherently supported by, this specification. Furthermore, the Applicant reserves the right to amend the claims to affirmatively disclaim features and characteristics that may be present in the prior art, even if those features and characteristics are not expressly described in this specification. Therefore, any such amendments will not add new matter to the specification or claims, and will comply with written description, sufficiency of description, and added matter requirements, including the requirements under 35 U.S.C. § 112(a) and Article 123(2) EPC.

Any numerical range recited in this specification describes all sub-ranges of the same numerical precision (i.e., having the same number of specified digits) subsumed within the recited range. For example, a recited range of "1.0 to 10.0" describes all sub-ranges between (and including) the recited minimum value of 1.0 and the recited maximum value of 10.0, such as, for example, "2.4 to 7.6," even if the range of "2.4 to 7.6" is not expressly recited in the text of the specification. Accordingly, the Applicant reserves the right to amend this specification, including the claims, to expressly recite any sub-range of the same numerical precision subsumed within the ranges expressly recited in this specification. All such ranges are inherently described in this specification such that amending to expressly recite any such sub-ranges will comply with written description, sufficiency of description, and added matter requirements, including the requirements under 35 U.S.C. § 112(a) and Article 123(2) EPC. Also, unless expressly specified or otherwise required by context, all numerical parameters described in this specification (such as those expressing values, ranges, amounts, percentages, and the like) may be read as if prefaced by the word "about," even if the word "about" does not expressly appear before a number. Additionally, numerical parameters described in this specification should be construed in light of the number of reported significant digits, numerical precision, and by applying ordinary rounding techniques. It is also understood that numerical parameters described in this specification will necessarily possess the inherent variability characteristic of the underlying measurement techniques used to determine the numerical value of the parameter.

The invention(s) described in this specification can comprise, consist of, or consist essentially of the various features and characteristics described in this specification. The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. Thus, a composition, coating, or process that "comprises," "has," "includes," or "contains" one or more features and/or characteristics possesses those one or more features and/or characteristics, but is not limited to possessing only those one or more features and/or characteristics. Likewise, an element of a composition, coating, or process that "comprises," "has," "includes," or "contains" one or more features and/or characteristics possesses those one or more features and/or characteristics, but is not limited to possessing only those one or more features and/or characteristics, and may possess additional features and/or characteristics.

The grammatical articles "a," "an," and "the," as used in this specification, including the claims, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and can be employed or used in an implementation of the described compositions, coatings, and processes. Nevertheless, it is understood that use of the terms "at least one" or "one or more" in some instances, but not others, will not result in any interpretation where failure to use the terms limits objects of the grammatical articles "a," "an," and "the" to just one. Further, the use of a singular noun includes the plural, and the use of a plural noun includes the singular, unless the context of the usage requires otherwise.

Any patent, publication, or other document identified in this specification is incorporated by reference into this specification in its entirety unless otherwise indicated, but only to the extent that the incorporated material does not conflict with existing descriptions, definitions, statements, illustrations, or other disclosure material expressly set forth in this specification. As such, and to the extent necessary, the express disclosure as set forth in this specification supersedes any conflicting material incorporated by reference. Any material, or portion thereof, that is incorporated by reference into this specification, but which conflicts with existing definitions, statements, or other disclosure material set forth herein, is only incorporated to the extent that no conflict arises between that incorporated material and the existing disclosure material. Applicant reserves the right to amend this specification to expressly recite any subject matter, or portion thereof, incorporated by reference. The amendment of this specification to add such incorporated subject matter will comply with written description, sufficiency of description, and added matter requirements, including the requirements under 35 U.S.C. § 112(a) and Article 123(2) EPC.

What is claimed is:

1. A curable composition comprising:
   a compound comprising a conjugated diene group; and
   a 1,1-di-activated vinyl compound, wherein the 1,1, di-activated vinyl compound comprises a diaryl methylene malonate, a multifunctional form of a dialkyl methylene malonate, a multifunctional form of a diaryl methylene malonate, or a combination thereof.

2. The curable composition of claim 1, wherein the 1,1-di-activated vinyl compound comprises:
   a multifunctional form of a dialkyl methylene malonate; or
   a multifunctional form of a diaryl methylene malonate; or
   a combination of any thereof.

3. The curable composition of claim 2, wherein the 1,1-di-activated vinyl compound comprises:
   a multifunctional form of diethyl methylene malonate comprising a transesterification adduct of diethyl methylene malonate and at least one polyol.

4. The curable composition of claim 3, wherein the transesterification adduct of diethyl methylene malonate and at least one polyol comprises a transesterification adduct of diethyl methylene malonate and a diol.

5. The curable composition of claim 4, wherein the diol comprises an alkane diol.

6. The curable composition of claim 5, wherein the alkane diol comprises 1,5-pentane diol and/or 1,6-hexanediol.

7. The curable composition of claim 1, wherein the compound comprising a conjugated diene groups comprises a polymer resin comprising pendant and/or terminal conjugated diene groups.

8. The curable composition of claim 7, wherein the resin comprises pendant and/or terminal open-chain conjugated diene groups.

9. The curable composition of claim 7, wherein the resin comprises pendant and/or terminal cyclic conjugated diene groups.

10. The curable composition of claim 9, wherein the resin comprises pendant and/or terminal cyclopentadiene groups.

11. The curable composition of claim 9, wherein the resin comprises pendant and/or terminal thiophene groups.

12. The curable composition of claim 9, wherein the resin comprises pendant and/or terminal pyrrole groups.

13. The curable composition of claim 9, wherein the resin comprises pendant and/or terminal furan groups.

14. The curable composition of claim 7, wherein the resin comprises a reaction product of a polyisocyanate and a conjugated diene compound comprising an active hydrogen group.

15. The curable composition of claim 7, wherein the resin comprises a reaction product of a polyol, polyamine, or polythiol and a conjugated diene compound comprising an isocyanate group.

16. The curable composition of claim 7, wherein the resin comprises a polyurethane resin, a polyurea resin, an acrylic resin, a polyester resin, a polycarbonate resin, a polysiloxane resin, an epoxy resin, a melamine resin, or a phenol formaldehyde resin, or a composite resin comprising a polymer comprising two or more backbone functionalities, or a combination of any thereof.

17. A coating composition comprising the curable composition of claim 1.

18. An adhesive or sealant composition comprising the curable composition of claim 1.

19. A process for applying a curable composition to a substrate comprising:
    applying the curable composition of claim 1 to at least a portion of a substrate; and
    curing the curable composition;
    wherein the curing comprises a crosslinking reaction between (1) the compound comprising a conjugated diene group and (2) the 1,1-di-activated vinyl compound, or a multifunctional form thereof, or a combination thereof.

20. The process of claim 19, wherein the crosslinking reaction comprises a pericyclic reaction.

21. The process of claim 19, wherein the crosslinking reaction comprises a cycloaddition reaction.

22. The process of claim 19, wherein the crosslinking reaction comprises a Diels-Alder reaction.

23. The process of claim 19, wherein the crosslinking reaction comprises a pericyclic reaction that occurs in a cascade with another chemical transformation.

24. A coating, adhesive, or sealant system comprising:
    a coating, adhesive, or sealant layer applied to at least a portion of a substrate, wherein the coating, adhesive, or sealant layer comprises a Diels-Alder addition reaction product of:
    a resin comprising pendant and/or terminal conjugated diene groups; and
    a 1,1-di-activated vinyl compound, wherein the 1,1, di-activated vinyl compound comprises a diaryl methylene malonate, a multifunctional form of a dialkyl methylene malonate, a multifunctional form of a diaryl methylene malonate, or a combination thereof.

25. The coating, adhesive, or sealant system of claim 24, wherein the 1,1-di-activated vinyl compound comprises a multifunctional form of a dialkyl methylene malonate, a multifunctional form of a diaryl methylene malonate, or a combination thereof.

26. The coating, adhesive, or sealant system of claim 25, wherein the 1,1-di-activated vinyl compound comprises:

a multifunctional form of diethyl methylene malonate comprising a transesterification adduct of diethyl methylene malonate and at least one polyol.

27. The coating, adhesive, or sealant system of claim 26, wherein the transesterification adduct of diethyl methylene malonate and at least one polyol comprises a transesterification adduct of diethyl methylene malonate and a diol.

28. The coating, adhesive, or sealant system of claim 27, wherein the diol comprises 1,5-pentane diol and/or 1,6-hexanediol.

29. The coating, adhesive, or sealant system of claim 24, wherein the resin comprises pendant and/or terminal open-chain conjugated diene groups.

30. The coating, adhesive, or sealant system of claim 24, wherein the resin comprises pendant and/or terminal cyclic conjugated diene groups.

31. The coating, adhesive, or sealant system of claim 24, wherein the resin comprises pendant and/or terminal cyclopentadiene groups, thiophene groups, pyrrole groups, or furan groups, or combinations of any thereof.

32. The coating, adhesive, or sealant system of claim 24, wherein the resin comprises a reaction product of a polyisocyanate and a conjugated diene compound comprising an active hydrogen group.

33. The coating, adhesive, or sealant system of claim 24, wherein the resin comprises a reaction product of a polyol, polyamine, or polythiol and a conjugated diene compound comprising an isocyanate group.

34. The coating, adhesive, or sealant system of claim 24, wherein the resin comprises a polyurethane resin, a polyurea resin, an acrylic resin, a polyester resin, a polycarbonate resin, a polysiloxane resin, an epoxy resin, a melamine resin, or a phenol formaldehyde resin, or a composite resin comprising a polymer comprising two or more backbone functionalities, or a combination of any thereof.

35. The coating, adhesive, or sealant system of claim 24, wherein the coating, adhesive, or sealant layer exhibits intumescence, delamination, or self-healing properties upon application of heat, radiation, pressure, and/or a catalyst composition.

36. An article comprising the coating, adhesive, or sealant system of claim 24 deposited on a surface of the article.

37. The article of claim 36, wherein the article comprises a vehicle component, an architectural component, or a component of a free-standing structure.

38. A process for treating a coating, adhesive, or sealant system comprising:
 applying heat, radiation, pressure, or a catalyst composition, or a combination of any thereof, to the coating, adhesive, or sealant system of claim 24;
 wherein the application of the heat, radiation, pressure, and/or a catalyst composition results in a retro-Diels-Alder reaction that breaks the addition reaction bonds between the resin and the 1,1-di-activated vinyl compound and reverses cure of the coating, adhesive, or sealant layer.

39. The process of claim 38, wherein the coating, adhesive, or sealant layer becomes intumescent upon the application of the heat, radiation, pressure, and/or a catalyst composition.

40. The process of claim 38, wherein the coating, adhesive, or sealant layer delaminates upon the application of the heat, radiation, pressure, and/or a catalyst composition.

41. The process of claim 38, wherein the coating, adhesive, or sealant layer becomes hand peel-able upon the application of the heat, radiation, pressure, and/or a catalyst composition.

42. The process of claim 38, wherein the coating, adhesive, or sealant system comprises a coating layer that exhibits self-healing properties upon the application of the heat, radiation, pressure, and/or a catalyst composition.

\* \* \* \* \*